US011083471B2

(12) United States Patent
Morris et al.

(10) Patent No.: US 11,083,471 B2
(45) Date of Patent: Aug. 10, 2021

(54) SYSTEMS AND METHODS FOR TRANSCORPOREAL MICRODECOMPRESSION

(71) Applicant: GLOBUS MEDICAL, INC., Audubon, PA (US)

(72) Inventors: Ross Morris, Norristown, PA (US); Neil Crawford, Chandler, AZ (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 108 days.

(21) Appl. No.: 16/660,135

(22) Filed: Oct. 22, 2019

(65) Prior Publication Data

US 2020/0121331 A1 Apr. 23, 2020

Related U.S. Application Data

(60) Provisional application No. 62/748,601, filed on Oct. 22, 2018.

(51) Int. Cl.
*A61B 17/17* (2006.01)
*A61B 17/16* (2006.01)
*A61B 34/20* (2016.01)
*A61B 34/00* (2016.01)

(52) U.S. Cl.
CPC ...... *A61B 17/1757* (2013.01); *A61B 17/1631* (2013.01); *A61B 17/1633* (2013.01); *A61B 17/1635* (2013.01); *A61B 17/1671* (2013.01); *A61B 17/17* (2013.01); *A61B 34/20* (2016.02); *A61B 34/70* (2016.02); *A61B 2034/2055* (2016.02)

(58) Field of Classification Search
CPC . A61B 17/1757; A61B 17/1671; A61B 34/20; A61B 17/17
See application file for complete search history.

(56) References Cited

U.S. PATENT DOCUMENTS

| | | | | |
|---|---|---|---|---|
| 5,484,437 A | * | 1/1996 | Michelson | A61F 2/446 606/86 A |
| 8,052,695 B2 | * | 11/2011 | Kienzle, III | A61B 17/1703 606/130 |
| 2003/0032962 A1 | * | 2/2003 | McGahan | A61F 2/4611 606/80 |
| 2004/0176763 A1 | * | 9/2004 | Foley | A61M 29/02 606/60 |
| 2006/0142657 A1 | * | 6/2006 | Quaid | A61B 34/76 600/424 |
| 2009/0099571 A1 | * | 4/2009 | Cresina | A61B 17/17 606/96 |

(Continued)

OTHER PUBLICATIONS

Lowry DW, et al. "Clinical Outcomes After Cervical Transcorporeal Microdecompression and Vertebral Body Access Channel Repair" Mar. 30, 2015, International Journal of Spine Surgery, vol. 9, pp. 1-6. (Year: 2015).*

*Primary Examiner* — Christian A Sevilla

(57) ABSTRACT

Devices, systems, and methods for performing a transcorporeal microdecompression are described. The transcorporeal microdecompression may include a bone void plug allograft and specialized instruments for performing the procedure. This procedure may be performed under navigation and/or with robotic assistance.

19 Claims, 12 Drawing Sheets

(56) References Cited

U.S. PATENT DOCUMENTS

| | | | | |
|---|---|---|---|---|
| 2009/0264940 A1* | 10/2009 | Beale | ................... | A61B 90/39 |
| | | | | 606/86 R |
| 2009/0312763 A1* | 12/2009 | McCormack | ...... | A61B 17/8822 |
| | | | | 606/83 |
| 2010/0087823 A1* | 4/2010 | Kondrashov | ........ | A61B 17/025 |
| | | | | 606/79 |

* cited by examiner

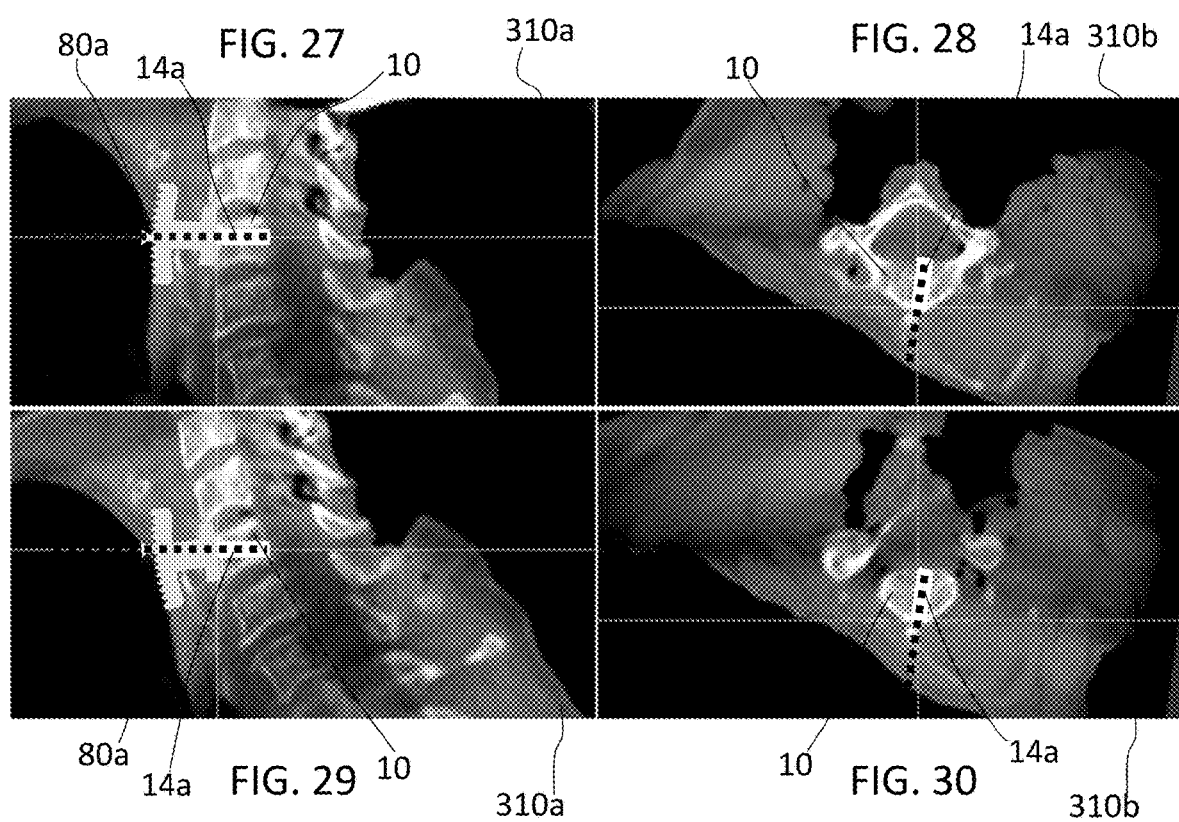

SYSTEMS AND METHODS FOR TRANSCORPOREAL MICRODECOMPRESSION

CROSS REFERENCE TO RELATED APPLICATIONS

This application is a non-provisional application that claims priority to U.S. Patent Application 62/748,601 filed on Oct. 22, 2018, which is incorporated in its entirety herein.

FIELD OF THE INVENTION

The present disclosure relates to surgical devices, systems, and methods for spinal procedures, and more particularly, devices, systems, and methods for spinal procedures involving transcorporeal microdecompression.

BACKGROUND OF THE INVENTION

Surgeons may perform a transcorporeal microdecompression procedure on the cervical spine to remove posterolateral pathologies, for example. The procedure may target the removal of one or more disc herniation fragments and/or osteophytes. This procedure may involve drilling a channel through the vertebral body to access the posterior corner of the vertebra near the pathology. As this procedure creates a void in the vertebral body, the surgeon may utilize a plug to fill the anterior half of the bone to restore some strength to the vertebral body. Some existing plugs may be made of a brittle ceramic that may be easily fractured and can be difficult to place.

There is a need for improved plugs, instruments, and/or other improvements to ease the performance and improve the outcome of the transcorporeal microdecompression procedure.

SUMMARY OF THE INVENTION

Embodiments of the present application are generally directed to devices, systems and methods for transcorporeal microdecompression. Although transcorporeal microdecompression procedures are exemplified herein, it will be appreciated that the devices, instruments and methods may be adapted or modified for other anatomical locations and procedures.

In accordance with the application, in some embodiments, an implant is provided for transcorporeal microdecompression. The implant may include a bone void plug extending from a first end to a second end. The first end may be configured to be inserted into a channel in a vertebra. The second end may have an opening configured to mate with an inserter instrument. A tapered side wall may connect the first and second ends, and a graft window may extend through the side wall. The tapered side wall may have a diameter greater at the second end relative to the first end to help prevent migration through the channel post-op. The implant may be a single-piece, allograft design.

In accordance with some embodiments, a dedicated inserter may be provided to more precisely insert the implant and provide for the possibility of removal. The inserter may have an outer sleeve, a middle sleeve terminating in a tip, the middle sleeve positioned within the outer sleeve, an inner shaft positioned within the middle sleeve, and an actuator configured to move the middle sleeve axially along a length of the inserter. The tip may be configured to mate with the opening in the implant such that when the actuator pushes the middle sleeve forward, the tip is compressed, but when moved back, the inner shaft forces the tip outward, thereby mating with the opening of the implant. The inserter tip and opening in the implant may form a circular dovetail connection.

In accordance with some embodiments, a uniplanar drill guide may be used to select the optimal angle for creating and/or access the channel in the vertebra. The uniplanar drill guide may have a base having a first extension portion and a second extension portion connected by a bridge portion. The first extension portion may extend upwardly and terminate in a first free end. The first free end may have a t-shape with a tooth array positioned on an upper surface of the first free end. The second extension portion may extend upwardly and terminate in a second free end, and the second extension portion may define a partially cylindrical cavity configured to guide a temporary fastener. The drill guide may include a fastener configured to temporarily secure the base to the vertebra. The drill guide may include a guide tube movable relative to the base. The guide tube has a central lumen configured to guide an instrument to create or access the channel in the vertebra. Movement of the guide tube may be controllable by an actuation mechanism having a rotating lock arm with a cam surface and a selector pin movable by the cam surface. The selector pin is configured to engage with one or more teeth of the tooth array on the base to thereby lock an angle of the guide tube. The actuation mechanism may include a linearly moveable pin controllable by a button. The rotating lock arm may include a first portion and a second portion provided substantially perpendicular to one another. The first portion may have an elongate opening for receiving the moveable pin, and the second portion may have the cam surface configured to move the selector pin.

In yet other embodiments, a fixed angle guide may be included to provide better stability during drilling and allow fine tuning of the channel in-situ. The fixed angle guide may include a base configured to be attached to the vertebral body using a temporary fixation pin or other fastener. The drill guide tube may be permanently attached to the base to set both the caudal and lateral angles. The drill guide includes a guide tube rigidly affixed to the base and an extension portion extending upwardly from the base and terminating at a free end. The extension portion may define a partially cylindrical cavity configured to guide the temporary fixation pin.

In yet further embodiments, a lockable and adjustable depth stop may be provided to ensure patient safety. The lockable depth stop may include an outer sleeve, an inner sleeve, and a lock collar. The depth stop may snap onto the shaft of an instrument, such as a drill, and the depth can be set by rotating the outer sleeve of the stop. The stop may include one or more spring fingers on the outer sleeve to engage with one or more indentations along the inner sleeve. The lock collar may snap between unlocked and locked positions.

In some embodiments, robotics systems and/or navigation may be used to aid the surgeon in the transcorporeal microdecompression procedure. A surgical robot system may include an array having a base configured to temporarily affix to a vertebra, an extension arm extending from the base and terminating in a fixed array having a plurality of markers, a guide tube, and a ball joint connecting the guide tube to the base. The ball joint may define a spherical hole and the guide tube may have a matching sphere that mates with the spherical hole. When the ball joint is locked, an angle of the guide tube is locked, thereby forming a targeted trajectory through the guide tube. The robot system includes a robot configured to track and/or navigate the array. The robot includes a camera configured to track the plurality of markers. The robot may be configured to determine the location and any movement of the markers. The robot may include a software program configured to determine a pre-planned angle for the guide tube using one or more pre-operative and/or interoperative CT and/or MRI scans.

According to further embodiments, methods of performing the transcorporeal microdecompression procedure may include one or more of the following steps: (1) using a robotic and/or navigation system to establish a pre-planned trajectory for a channel into a vertebra; (2) using a robotic and/or navigation system to position a guide tube along the pre-planned trajectory; (3) creating a channel along the pre-planned trajectory using the guide tube to form the channel from the anterior to the posterior side of the vertebra; (4) cleaning out the channel and/or decompressing the spine; and (5) inserting an implant into the channel created during the procedure.

Also provided are kits including implants or plugs of varying shapes and sizes, plates of varying shapes and sizes, fasteners of varying types and sizes, drill guides, drill depth stops, and other components for installing the same and performing the transcorporeal microdecompression procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 27 depicts a sagittal view of a CT scan with computer graphics overlaid to help the user select the appropriate detent for the uniplanar drill guide from a surgical planning screen according to one embodiment;

FIG. 28 depicts an axial view of the CT scan of FIG. 27;

FIG. 29 depicts a sagittal view with the graphic having a different trajectory and detent for the uniplanar guide than FIG. 27; and FIG. 30 depicts an axial view of FIG. 29.

DETAILED DESCRIPTION OF THE INVENTION

Embodiments of the present application are generally directed to devices, systems and methods for transcorporeal microdecompression. Some embodiments are directed to bone void plugs implants configured to accept an insertion instrument. In one exemplary embodiment, an implant inserter is a dedicated tool that can be used to more precisely insert the bone void plug implant. Some embodiments are directed to instruments, such as a uniplanar drill guide configured to be placed flush with and centered on the anterior wall of the patient's vertebral body, thereby minimizing the amount of cephalad/caudal toggle. Yet other embodiments are directed to other improvements including a pre-assembled guide, lockable depth stop, or other suitable devices and instruments to assist with the transcorporeal microdecompression. Some embodiments are directed to robotics systems and/or navigation equipment and techniques to improve the transcorporeal microdecompression procedure and results.

Although devices, instruments, and methods are described herein for transcorporeal microdecompression, it will be appreciated that the devices, instruments, and methods may be adapted for one or more different anatomical areas and/or different surgical procedures.

Figure 1:
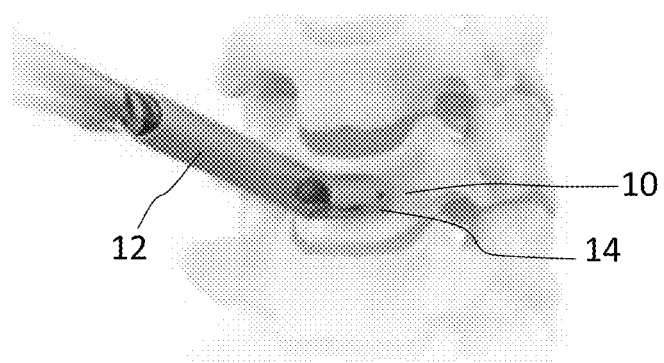
FIG. 1 is an AP view of a tool for creating an access channel in the anterior aspect of a vertebra according to one embodiment.
Figure 2:
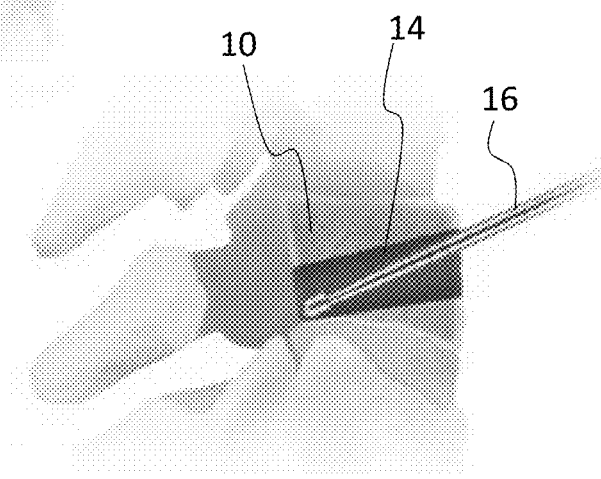
FIG. 2 is a lateral view of a tool for burring a posterior wall of the vertebra according to one embodiment.
Figure 3:
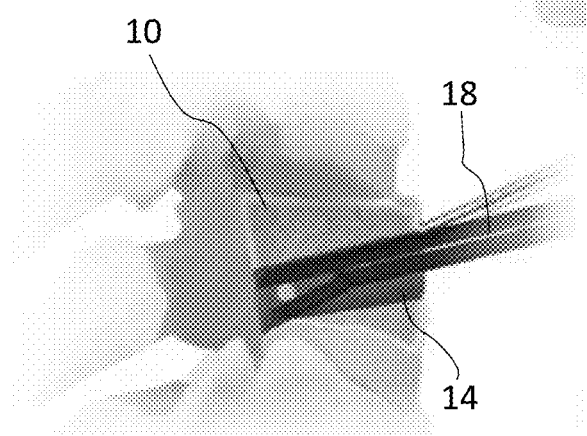
FIG. 3 is a lateral view of a tool for decompressing the spine according to one embodiment.
Figure 4:
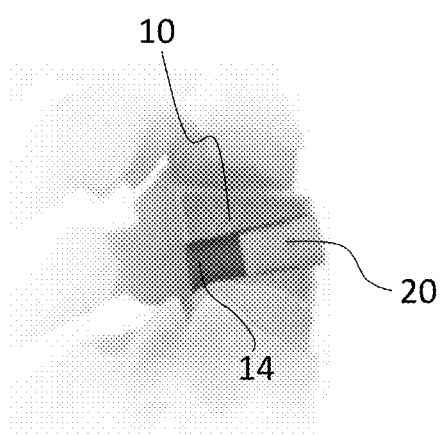
FIG. 4 is a lateral view of a bone void plug implant inserted into the opening in the vertebra created in FIGS. 1-3 according to one embodiment.

According to one embodiment, transcorporeal microdecompression may be a procedure that allows for early surgical intervention to address early stage herniation and/or stenosis. Transcorporeal microdecompression may target the removal of one or more disc herniation fragments and/or osteophytes through anterior access to the vertebral foramen. FIGS. 1-4 depict a method suitable for performing the transcorporeal microdecompression procedure. FIG. 1 depicts an AP view of a cervical vertebra 10. In FIG. 1, a first instrument 12 may be used to create an access channel 14 through the vertebral body 10. The first instrument 12 may include a drill, guide, harvesting mill, and/or other instruments suitable to create the channel 14. The access channel 14 may extend from the anterior to the posterior side of the vertebra 10. FIG. 2 depicts a lateral view of the cervical vertebra 10. A second instrument 16 may be used to burr the posterior wall of the vertebra 10. In FIG. 3, a third instrument 18 may be used to decompress the spine. The third instrument 18 may include a dissector, kerrision, decker rongeur, curette or other instrument suitable for performing a discectomy and removing fragments and/or osteophytes. After the channel 14 is created, cleaned out, and the spine is decompressed, an implant or plug 20 may be inserted into the channel 14 to fill at least a portion of the void. As shown, the implant or plug 20 may fill the anterior portion of the channel 14. This procedure may be used independently or in conjunction with other techniques. For example, one or more spine fixation plates or integrated plate systems may be used on one or more adjacent levels of the spine.

Figure 5:
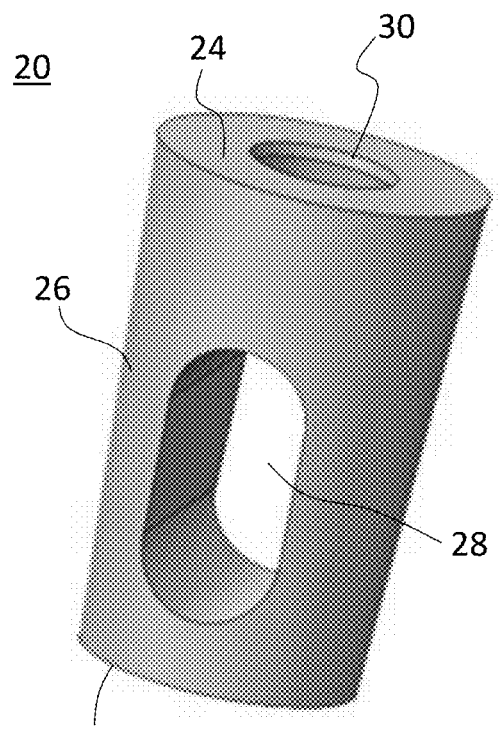
FIG. 5 is a perspective view of a bone void plug allograft according to one embodiment.
Figure 6:
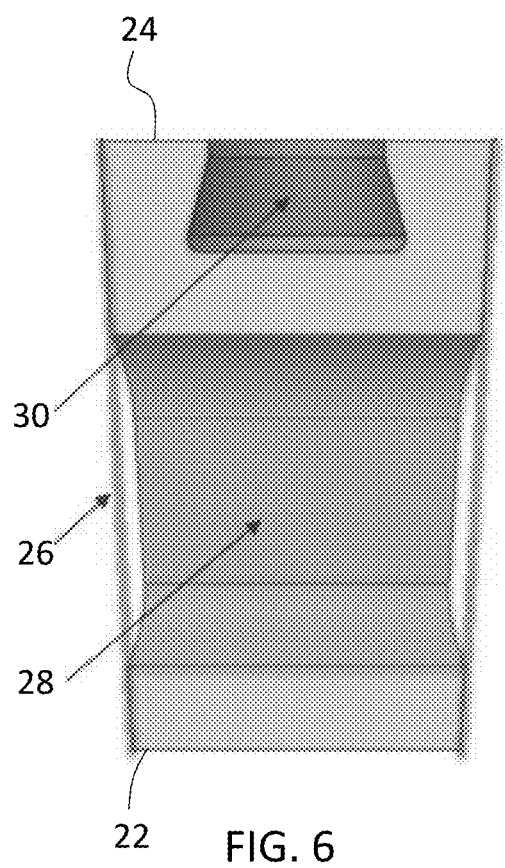
FIG. 6 is a cross-sectional view of the bone void plug allograft shown in FIG. 5.
Figure 10:
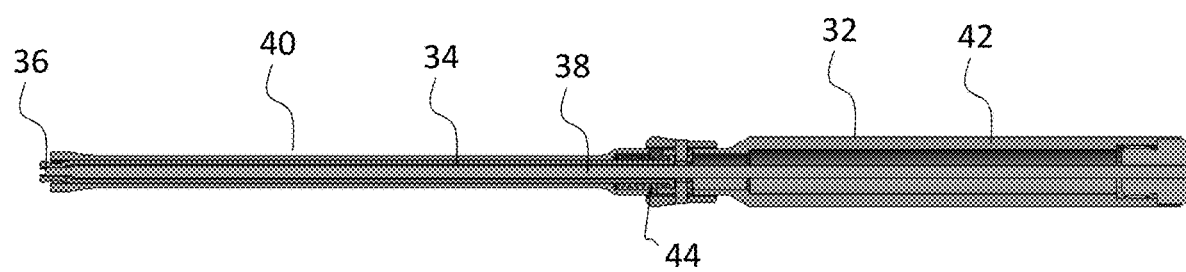
FIG. 10 is a cross-sectional view of an inserter instrument according to one embodiment.

Turning now to FIGS. 5 and 6, the implant or plug 20 may be a bone void plug allograft. Unlike prior plugs made from brittle ceramic that easily fracture, plug 20 may be made of stronger allograft. The bone void plug 20 may be a single piece, allograft design having a tapered wall 26, a graft window 28 perpendicular to the cone's axis, and an inserter interface 30 configured to accept an insertion instrument 32 (e.g., as shown in FIG. 10). The plug 20 may extend from a first end 22 to a second end 24. The first end 22 may be configured to be inserted into the channel 14. The second end 24 may be configured to connect to an insertion instrument 32. Although an allograft implant may be desired, it is possible that other suitable materials, such as PEEK (polyetheretherketone), may also be selected to make the implant.

A tapered side wall 26 connects the first and second ends 22, 24. The second end 24 may have a larger diameter than the first end 22. The tapered angle of side wall 26 may help to prevent migration of the implant 20 post-op. In particular, the tapered wall 26 may prevent the plug 20 from migrating through the drilled channel 14 as the larger diameter of the plug 20 may be oversized with respect to the channel 14. The taper may be up to 60 inclusive (3° per side from central axis), which is considered a locking taper and may help hold the plug 20 in place. The tapered design may help prevent migration through the channel 14, thereby avoiding compression of the neural elements. The graft window 28 facilitates fusion through the plug 20 to help incorporate or connect the allograft plug 20 to the patient's vertebral body. The graft window 28 may be filled with harvested autograft or allograft, for example.

Figure 7:
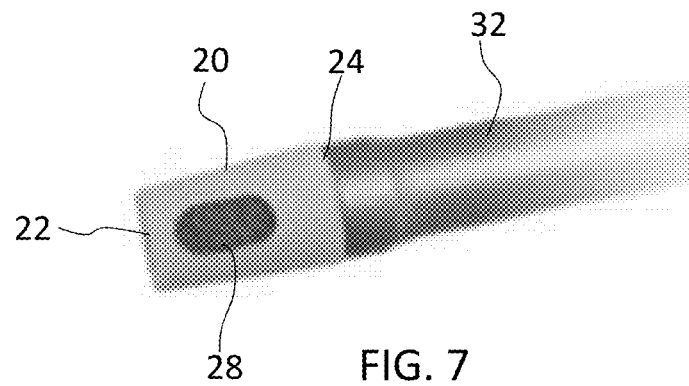
FIG. 7 is a close-up view of the bone void plug allograft attached to an inserter tool according to one embodiment.
Figure 8:
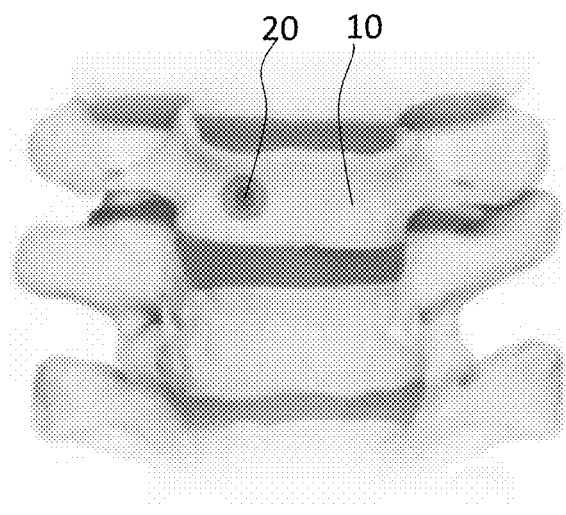
FIG. 8 is an AP view of the bone void plug allograft positioned within the void of the vertebra according to one embodiment.
Figure 9:
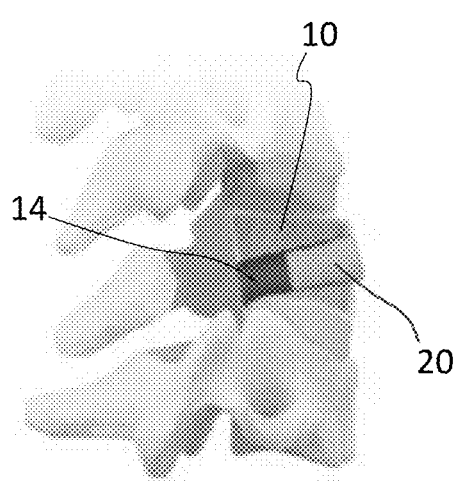
FIG. 9 is a lateral view of FIG. 8.

The second end 24 of the plug 20 may include a recess or opening 30 configured to engage with an insertion instrument 32. The recess or opening 30 may have a dovetail-type configuration (e.g., a circular dovetail) or other configuration for engaging the insertion instrument 32. The inserter connection feature provides for proper placement of the plug 20 and for the ability to remove the plug 20, if necessary. With emphasis on FIGS. 7-9, the inserter 32 is configured to place plug 20 within the channel 14 in bone. If necessary, a mallet may be used to gently tap the proximal end of the inserter 32 until the plug 20 is fully inserted. The anterior portion of the plug 20 should be flush with or slightly proud of the anterior wall of the vertebral body 10. FIG. 8 depicts an AP view of the bone void plug 20 positioned within the void of the vertebra 10 and FIG. 9 is a lateral view of FIG. 8. Once the plug 20 is in the desired position, the inserter 32 may be released and removed.

Figure 11:
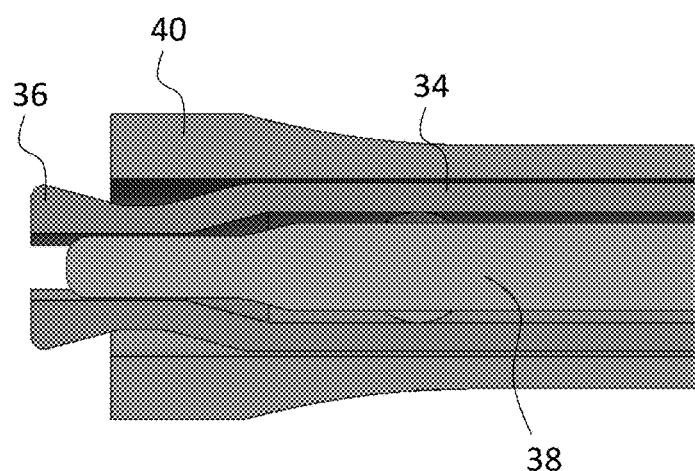
FIG. 11 is a close-up cross-sectional view of the distal end of the inserter of FIG. 10.

Turning now to FIGS. 10 and 11, the implant inserter 32 is shown in accordance with one embodiment. The implant inserter 32 may be a dedicated tool that can be used to more precisely insert the implant or plug 20. The inserter 32 may be configured to engage with the connection feature 30 of the plug 20, thereby allowing for proper placement of the plug 20 and/or the ability for removal of the plug 20. The inserter interface feature 30 allows for the implant 20 to firmly seat against the inserter 32 so that impaction forces are equally distributed to the implant 20. This feature 30 also allows for pulling on the implant 20 to move it towards the surgeon (e.g., if over-inserted) or remove the implant 20 completely from the channel 14.

The inserter 32 includes a handle portion 42, an outer tube or sleeve 40, an inner shaft 38, a tube or middle sleeve 34, and an actuator spring mechanism 44 configured to move the middle sleeve 34 axially along the length of the inserter 32. The middle sleeve 34 terminates in a dovetail tip 36 configured to mate with and match the corresponding opening 30 in the implant 20. The tip 36 is split and naturally compressed to minimize friction/interference when attaching and/or removing the implant 20. When the actuator 44 pushes the sleeve 34 forward, the tip 36 is compressed, but when sprung back, the inner shaft 38 forces the dovetail tip 36 to its nominally dimensioned position, thereby matching and mating with the opening 30 of the implant 20. The outer sleeve 40 acts as the backstop and ensures distributed force during insertion, helping ensure the implant 20 does not break loose.

Turning now to FIGS. 12-16, a uniplanar drill guide 50 is shown in accordance with one embodiment. More traditional drill guides may limit the surgeon to one angle during the procedure, which may not be applicable to every patient. To lessen the quantity of single angle drills guides needed, the uniplanar drill guide 50 allows the surgeon to select the optimal angle in-situ based on the patient's anatomy. The selected angle is locked in position unless the user releases it.

Figure 12:
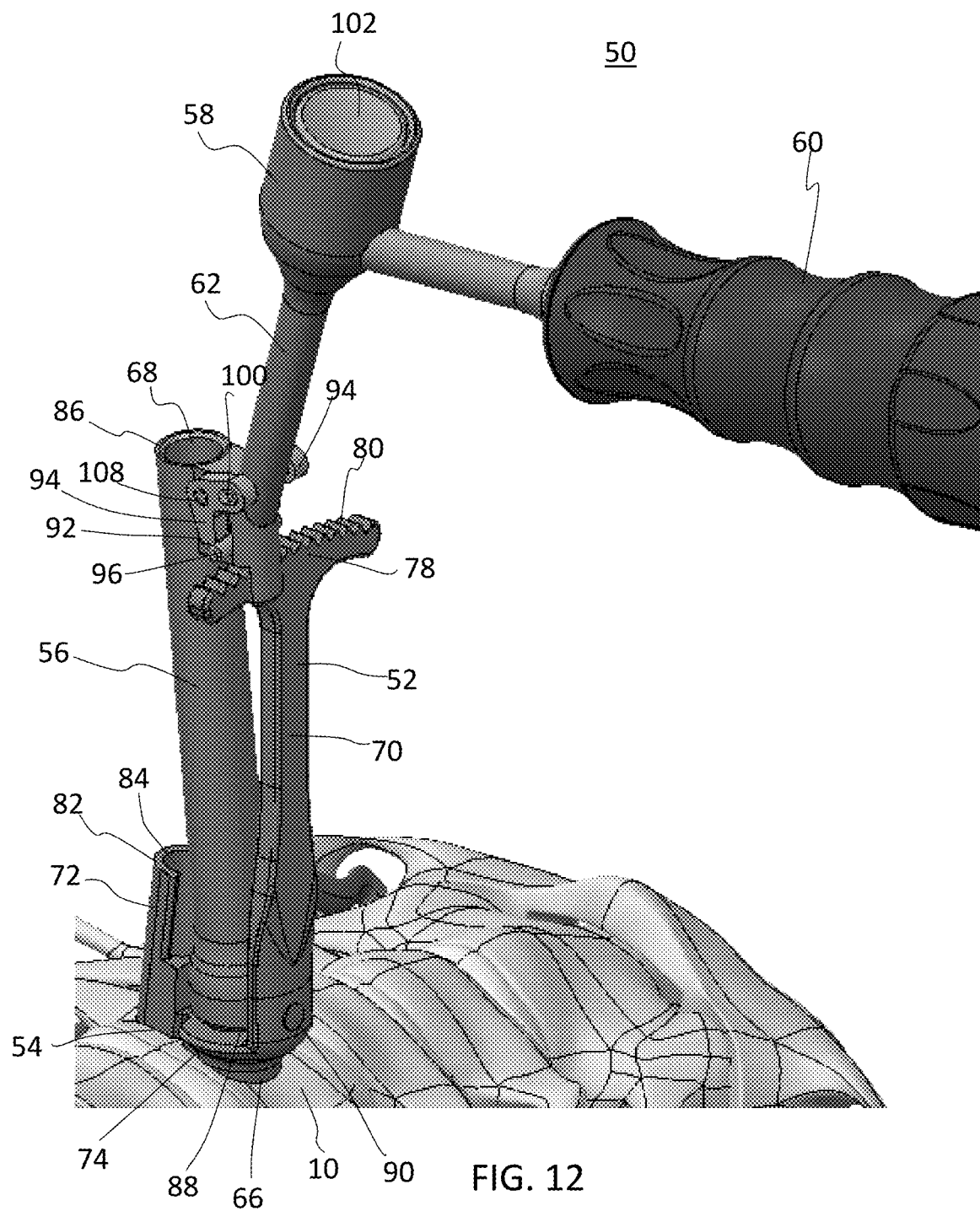
FIG. 12 is a perspective view of a uniplanar drill guide according to one embodiment.
Figure 13:
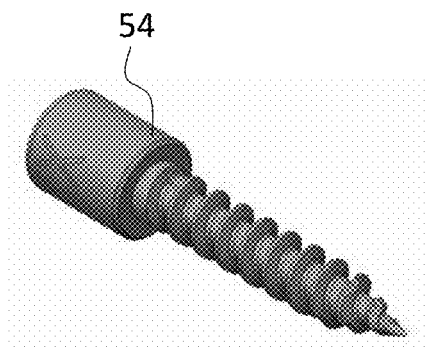
FIG. 13 is a temporary fastener suitable for use with the uniplanar drill guide of FIG. 12.

As shown in FIG. 12, the uniplanar drill guide 50 includes a base 52, a temporary fastener 54 configured to temporarily secure the base 52 to bone, a guide tube 56 movable relative to the base 52, the guide tube 56 having a central lumen 68 configured to guide a drill or other instrument to create and/or access the cavity or channel 14 in the bone, and a handle assembly 58 configured to control the uniplanar drill guide 50. The handle assembly 58 may include a handle 60 configured to be gripped by a surgeon or other operator and at least one arm 62 for engaging with and controlling the base 52 and the tube 56.

Figure 14:
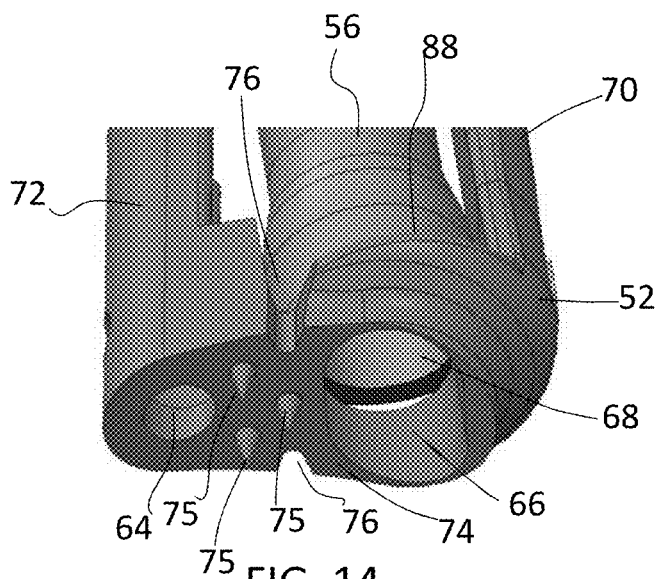
FIG. 14 is a close-up view of the bottom of the base of the uniplanar drill guide of FIG. 12.

The uniplanar drill guide base 52 includes a first portion 70 and a second portion 72 connected by a bridge portion 74. The bridge portion 74 has one or more surfaces configured to engage with the anatomy of the anterior surface of the vertebra 10. The uniplanar drill guide base 52 may be placed flush with and centered on the anterior wall of the patient's vertebral body 10, thus minimizing the amount of cephalad/caudal toggle. As best seen in FIG. 14, the base 52 may be anchored in place, for example, through a first opening 64 with a temporary fixation screw, pin, or other fastener 54. The base 52 may include a second opening 66 configured to be aligned with the lumen 68 through guide tube 56. The base 52 may be anchored in place, additionally or alternatively, for example, with one more spikes 75 protruding downwardly from the bridge portion 74. Thus, the base 52 may be rotationally stabilized with the small spikes 75 on the bottom surface of the bridge portion 74 that engages with the vertebra 10. Although three pointy spikes 75 are exemplified in FIG. 14, it will be appreciated that any suitable type, numbers, or placement of spikes 75 or other protrusions may be selected to improve fixation to the bone.

The uniplanar drill guide base 52 may include one or more indentations 76 along the bridge portion 74. If present, the separation of the first and second portions 70, 72 by one or more indentations 76 may allow for contouring of the bottom surface of bridge portion 74 to further accommodate the anatomy of the bone. As best seen in FIG. 12, the first portion 70 of the uniplanar drill guide 50 extends upwardly and terminates in a first free end 78. The free end 78 may form a t-shape and an upper surface of the free end 78 may include a radial ratchet or tooth array 80. The tooth array 80 may include a plurality of teeth, notches, or detents. The second portion 72 of the uniplanar drill guide 50 extends upwardly and terminates in a second free end 82. The second portion 72 may define a partially cylindrical cavity 84 configured to guide the fixation pin or fastener 154 into position and/or receive a portion of the guide tube 56 to thereby act as a stop when the guide tube 56 is articulated away from first portion 70.

The guide tube 56 extends from a proximal end 86 to a distal end 88 which engages and cooperates with base 52. A protrusion, pin 90, or other suitable mechanism may be used to secure the distal end 88 of the tube 56 to the base 52. Movement of the proximal end 86 of the guide tube 56 is controlled by an actuation mechanism 92. The actuation mechanism 92 includes a rotating lock arm 94, a selector pin 96 having a tip 98 configured to engage with one or more teeth of the tooth array 80 on the base 52, and a moveable pin 100 controllable by a button 102.

Figure 15:
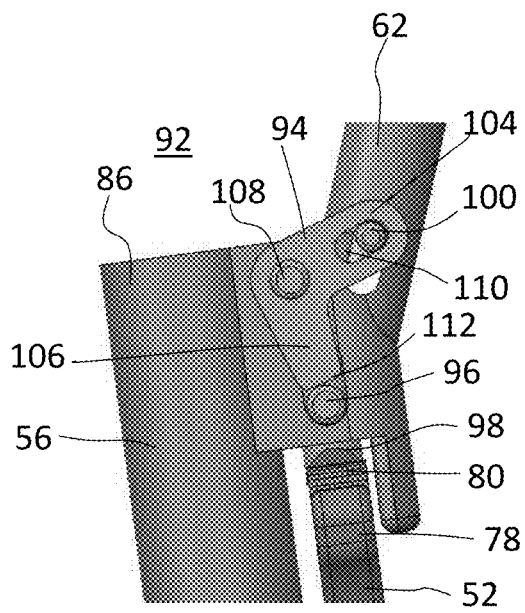
FIG. 15 is a side view of the mechanism for rotating the lock arm of the uniplanar drill guide in a natural, locked state.
Figure 16:
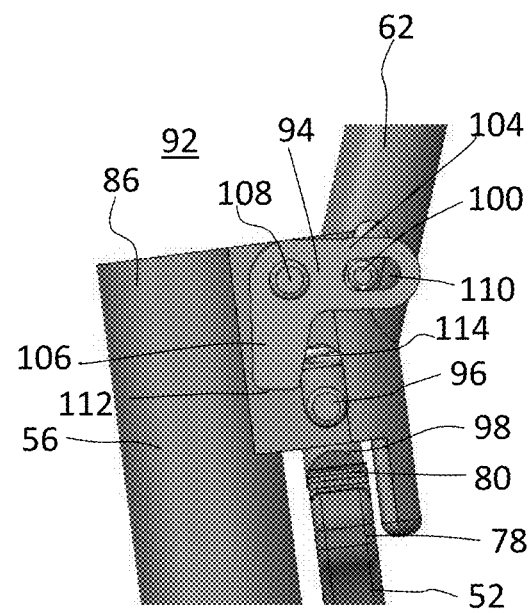
FIG. 16 is a side view of the mechanism for rotating the lock arm of the uniplanar drill guide in an unlocked state.

As best seen in FIGS. 15 and 16, the rotating lock arm 94 may include a first portion 104 and a second portion 106 provided substantially perpendicular to one another. The rotating lock arm 94 may be pivotable about a pivot pin 108. The first portion 104 may include an elongate opening 110 configured to receive the moveable pin 100 and the second portion 106 may include a cam surface 112 configured to move selector pin 96. The moveable pin 100 may be linearly translatable along an axial direction of arm 62 by button 102. The selector pin 96 may be spring loaded by a spring 114 and linearly translatable from a first position (shown in FIG. 15) to a second position (shown in FIG. 16). When the selector pin 96 is in the first position shown in FIG. 15, the rotating lock arm 94 is in a natural, locked state, and the selector pin 96 is engage with one or more teeth of the tooth array 80, thereby locking the position of the guide tube 56. When the selector pin 86 is in the second position shown in FIG. 16, the rotating locking arm 94 is in an unlocked state, and the guide tube 56 is free to move.

The guide tube 56 may have a fixed lateral angle, for example, of 7.5°. The cephalad/caudal angle may be set in-situ by the actuation mechanism 92. During operation, by pressing the lock button 102, the rotating lock arm 94 is actuated, thereby freeing the selector pin 96, and moving the distal tip 98 across the radial ratchet/tooth array 80. The selector pin 96 is spring loaded to provide tactile feedback when crossing the teeth 80, adjusting the angle of the guide tube 56, and to center the guide tube 56 at a lockable angle. Releasing the lock button 102 springs the rotating lock arm 94 back in place, preventing the selector pin 96 from moving and thus locking the angle of the guide tube 56. The surgeon can set the angle of the guide tube 56, confirm the trajectory with fluoroscopy, readjust the angle if necessary, and confidently drill an optimal angle for various patients.

The uniplanar guide 50 allows for in-situ angle adjustments to set the cephalad/caudal trajectory of the drill while maintaining a constant lateral angle, which provides a single instrument to set the optimal channel trajectory regardless of patient anatomy. The angle is locked unless the unlock button 102 is pressed.

Figure 17:
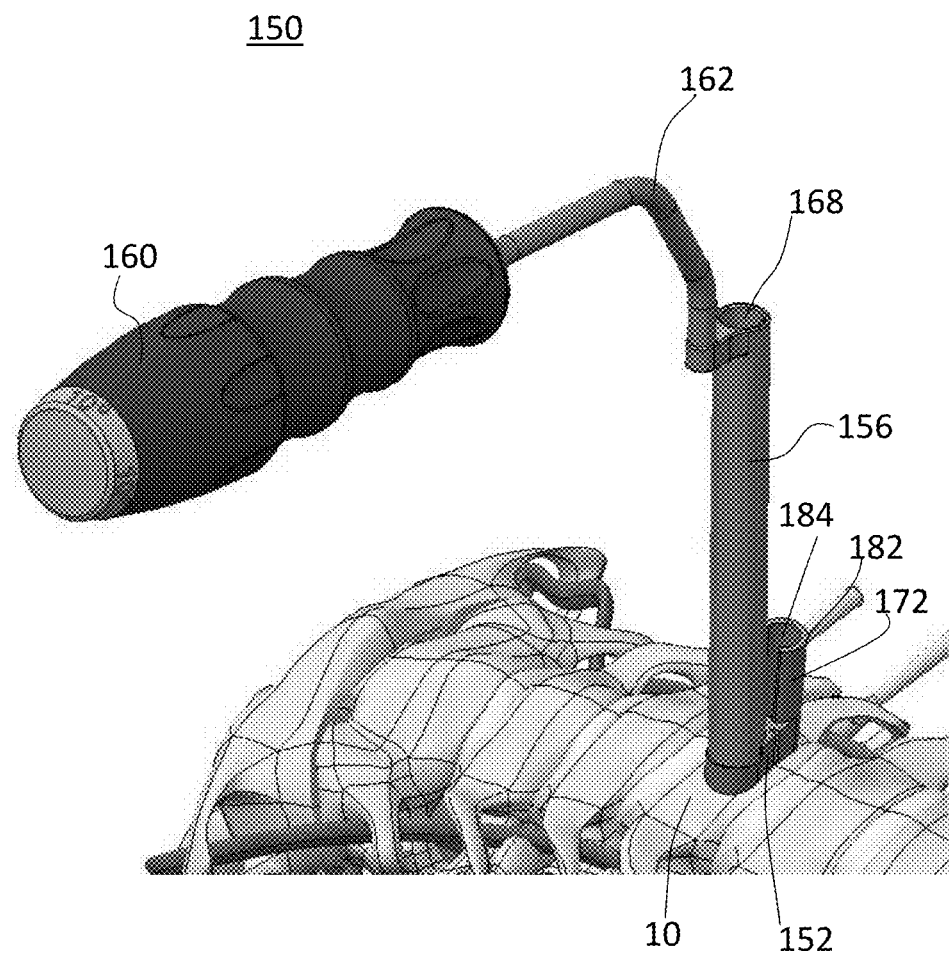
FIG. 17 is a perspective view of a pre-assembled fixed angle guide according to another embodiment.

As an alternative to the uniplanar drill guide 50, a fixed angle drill guide 150 is shown in FIG. 17. The fixed angle guide 150 may be suitable for some patient anatomy when a fixed guide tube 156 is desired. The fixed angle guide 150 has a base 152 configured to attach to the vertebral body using a temporary fastener 54, one or more spikes 75, and/or other suitable fasteners. The drill guide tube 156 is permanently attached to the base 152 to set both the caudal and lateral angles. An offset handle 160 is permanently attached to the guide tube 156 to ease installation into the patient, provide better stability during drilling, and/or allow fine tuning of the channel 14 in-situ.

The drill guide 150 includes base 152, fastener 54 configured to secure the base 152 to bone, guide tube 156 rigidly affixed to the base 152, the guide tube 156 having a central lumen 168 configured to guide a drill or other instrument to create and/or access the cavity or channel 14 in the bone, and handle 160 configured to be gripped by a surgeon or other operator and at least one arm 162 for controlling the base 152 and the tube 156. The guide base 152 may be placed flush with and centered on the anterior wall of the patient's vertebral body 10. An extension portion 172 of the guide 150 may extend upwardly from the base 152 and terminate at a free end 182. The extension portion 172 may define a partially cylindrical cavity 184 configured to guide the temporary fixation pin or fastener 154 into position.

Figure 18:
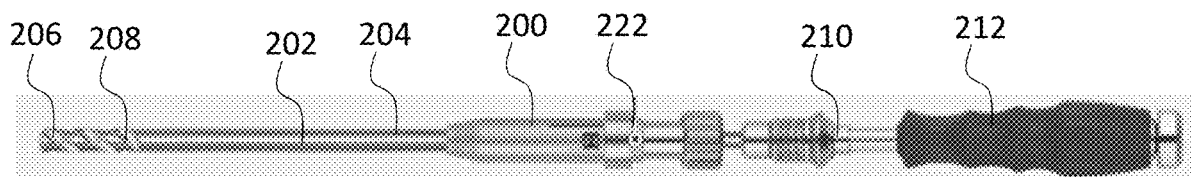
FIG. 18 is a side view of a lockable depth stop positioned on a drill according to one embodiment.
Figure 19:
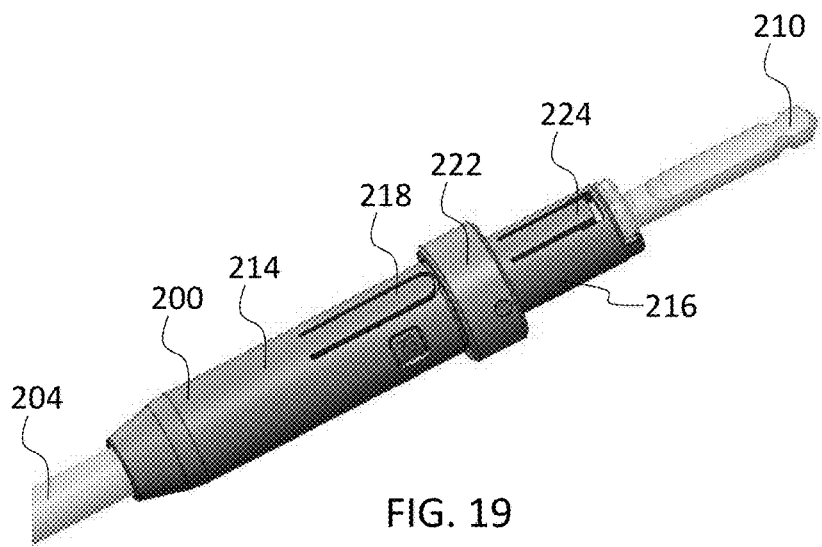
FIG. 19 is a close-up perspective view of the lockable depth stop of FIG. 18.
Figure 20:
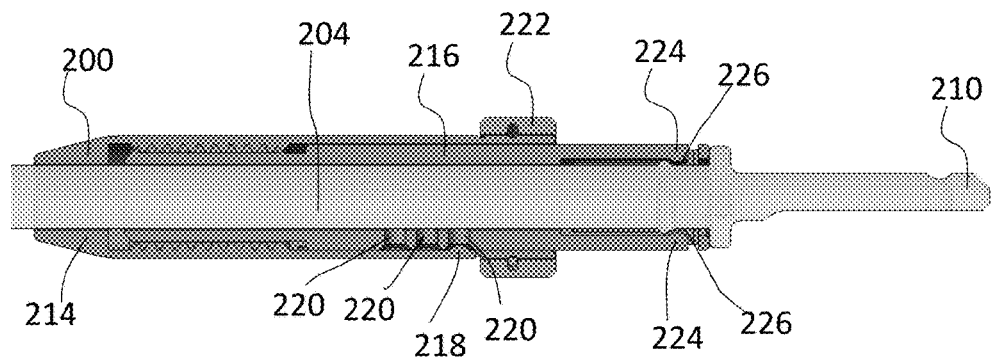
FIG. 20 is a close-up cross-sectional view of the lockable depth stop of FIG. 19.

Turning now to FIGS. 18-20, a lockable depth stop 200 may be used with a drill 202, harvesting mill, or other instrument to ensure the surgeon or user does not pass a given depth when creating and/or accessing channel 14. The depth stop 200 thereby prevents unintentional entry into the spinal canal or other restricted anatomical areas. The drill 202 may comprise a shaft 204 terminating at a distal end 206 with one or more threads 208 configured to cut bone, and a proximal end 210 configured to quick connect to a handle 212 having a grip for the surgeon or user. The depth stop 200 includes an outer sleeve 214, an inner sleeve 216, and a lock collar 222.

Figure 21:
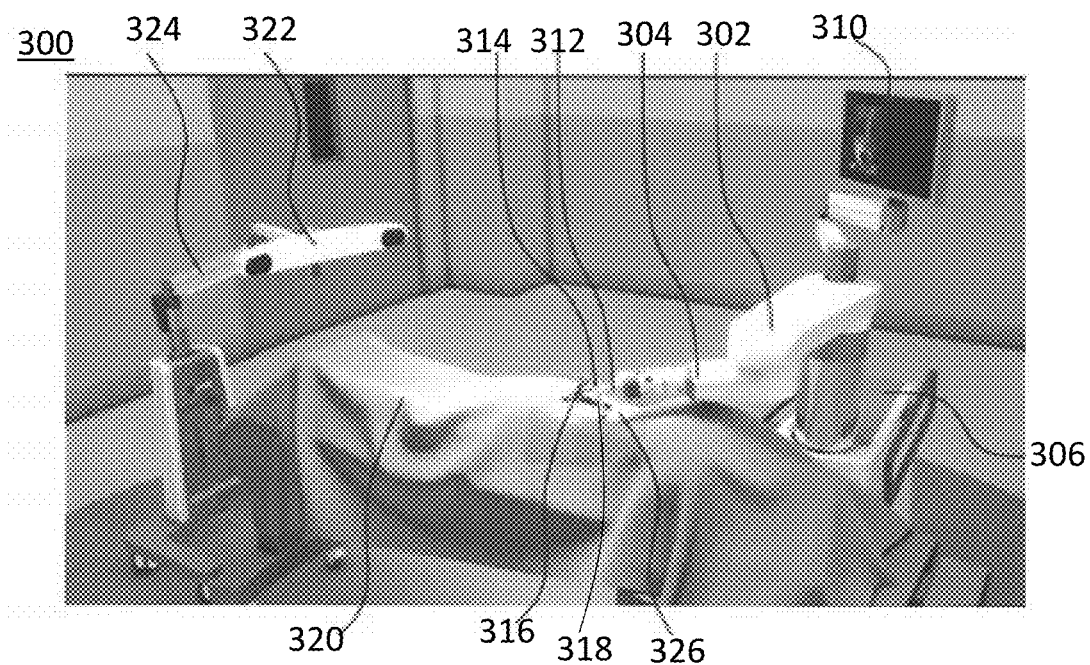
FIG. 21 illustrates a robotic and/or navigational system suitable for assisting with transcorporeal microdecompression procedures.
Figure 22:
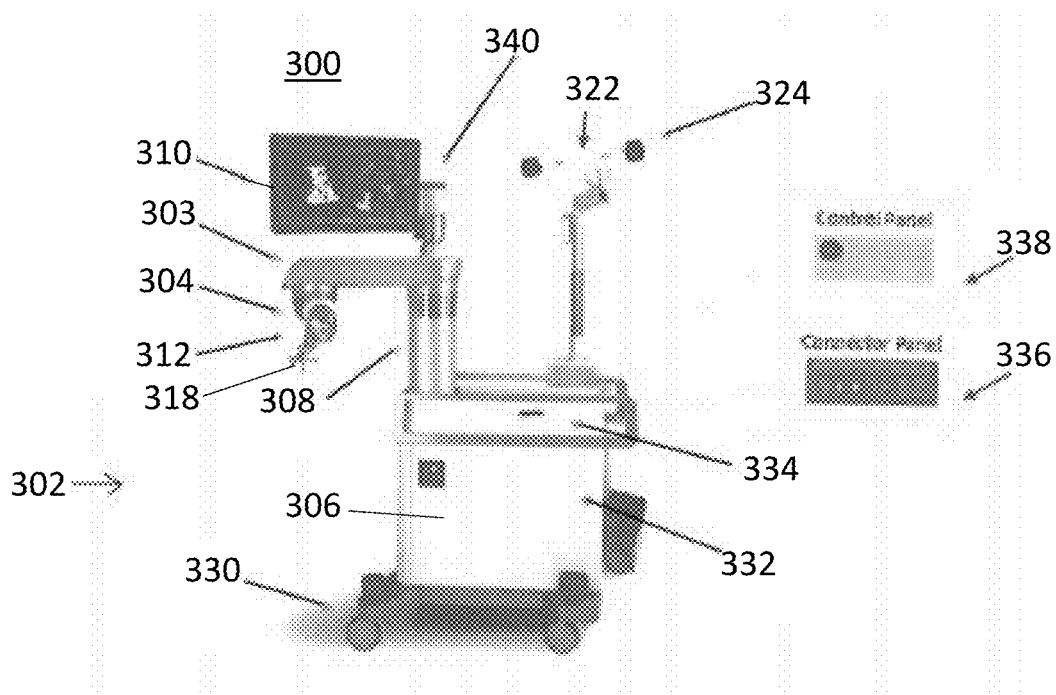
FIG. 22 further illustrates the surgical robotic system of FIG. 21 in accordance with an exemplary embodiment.

The drill depth stop 200 snaps onto the shaft 204 of the drill 212 and the depth can be set by rotating the outer sleeve 214 of the stop 200. One or more spring fingers 218 on the outer sleeve 214 rides between one or more indentations or holes 220 in the inner sleeve 216, designating various maximum depths for the drill 202. One or more spring fingers 224 on the inner sleeve 216 engages with corresponding indentations or notches 226 along the shaft 204 of the drill 202. The lock collar 222 snaps between unlocked and locked position, thereby allowing the user to select a depth and ensure it does not adjust during use. By sliding the lock collar 222 towards the handle 212, the depth stop 200 is unlocked, and by sliding the lock collar 222 towards the distal end 206, the depth stop is locked. The depth stop 200 may be adjusted in situ, and may be used to further ensure patient safety Robotics systems and/or navigation may be used to aid the surgeon in the transcorporeal microdecompression procedure. Turning now to FIGS. 21 and 22, a robot system 300 is shown, which may be suitable for use with transcorporeal microdecompression. The ability to perform this procedure under navigation and/or robotic assistance may help to target the pathology directly from imaging based on the best angle trajectory for the patient.

As seen in FIG. 21, the surgical robot system 300 may include, for example, a surgical robot 302, one or more robot arms 304, a base 306, a display 310, an end-effector 312, for example, including a guide tube 314, and one or more tracking markers 318. The surgical robot system 300 may include a patient tracking device 316 also including one or more tracking markers 318, which is adapted to be secured directly to the patient 320 (e.g., to the bone of the patient 320). The surgical robot system 300 may also utilize a camera 322, for example, positioned on a camera stand 324. The camera stand 324 can have any suitable configuration to move, orient, and support the camera 322 in a desired position. The camera 322 may include any suitable camera or cameras, such as one or more infrared cameras (e.g., bifocal or stereophotogrammetric cameras), able to identify, for example, active and passive tracking markers 318 in a given measurement volume viewable from the perspective of the camera 322. The camera 322 may scan the given measurement volume and detect the light that comes from the markers 318 in order to identify and determine the position of the markers 318 in three-dimensions. For example, active markers 318 may include infrared-emitting markers that are activated by an electrical signal (e.g., infrared light emitting diodes (LEDs)), and passive markers 318 may include retro-reflective markers that reflect infrared light (e.g., they reflect incoming IR radiation into the direction of the incoming light), for example, emitted by illuminators on the camera 322 or other suitable device.

FIG. 21 illustrates a potential configuration for the placement of the surgical robot system 300 in an operating room environment. For example, the robot 302 may be positioned near or next to patient 320. Although depicted near the head of the patient 320, it will be appreciated that the robot 302 can be positioned at any suitable location near the patient 320 depending on the area of the patient 320 undergoing the operation. The camera 322 may be separated from the robot system 302 and positioned at the foot of patient 320. This location allows the camera 322 to have a direct visual line of sight to the surgical field 326. Again, it is contemplated that the camera 322 may be located at any suitable position having line of sight to the surgical field 326. In the configuration shown, the surgeon may be positioned across from the robot 302 but is still able to manipulate the end-effector 312 and the display 310.

With respect to the other components of the robot 302, the display 310 can be attached to the surgical robot 302 and in other exemplary embodiments, display 310 can be detached from surgical robot 302, either within the surgical room with the surgical robot 302, or in a remote location. End-effector 312 may be coupled to the robot arm 304 and controlled by at least one motor or may be separate from the robot 302 and navigated by the surgeon. In exemplary embodiments, end-effector 312 can comprise a guide tube 314, which is able to receive and orient a surgical instrument used to perform surgery on the patient 320. Although generally shown with a guide tube 314, it will be appreciated that the end-effector 312 may be replaced with any suitable instrumentation suitable for use in surgery. In some embodiments, end-effector 312 can comprise any known structure for effecting the movement of the surgical instrument in a desired manner.

When affixed to the robot 302, the surgical robot 302 is able to control the translation and orientation of the end-effector 312. The robot 302 is able to move end-effector 312 along x-, y-, and z-axes, for example. The end-effector 312 can be configured for selective rotation about one or more of the x-, y-, and z-axis, and a Z Frame axis (such that one or more of the Euler Angles (e.g., roll, pitch, and/or yaw) associated with end-effector 312 can be selectively controlled). In some exemplary embodiments, selective control of the translation and orientation of end-effector 312 can permit performance of medical procedures with significantly improved accuracy compared to conventional robots that utilize, for example, a six degree of freedom robot arm comprising only rotational axes. For example, the surgical robot system 300 may be used to operate on patient 320, and robot arm 304 can be positioned above the body of patient 320, with end-effector 312 selectively angled relative to the z-axis toward the body of patient 302.

In some exemplary embodiments, the position of the surgical instrument can be dynamically updated so that surgical robot 302 can be aware of the location of the surgical instrument at all times during the procedure. Consequently, in some exemplary embodiments, surgical robot 302 can move the surgical instrument to the desired position quickly without any further assistance from a physician (unless the physician so desires). In some further embodiments, surgical robot 302 can be configured to correct the path of the surgical instrument if the surgical instrument strays from the selected, preplanned trajectory. In some exemplary embodiments, surgical robot 302 can be configured to permit stoppage, modification, and/or manual control of the movement of end-effector 312 and/or the surgical instrument. Thus, in use, in exemplary embodiments, a physician or other user can operate the system 300, and has the option to stop, modify, or manually control the autonomous movement of end-effector 312 and/or the surgical instrument. Further details of surgical robot system 300 including the control and movement of a surgical instrument by surgical robot 302 can be found in U.S. Patent Publication No. 2017/0239007, which is incorporated herein by reference in its entirety for all purposes.

The robotic surgical system 300 can comprise one or more tracking markers 318 configured to track the movement of robot arm 304, end-effector 312, patient 320, and/or the surgical instrument in three dimensions. In exemplary embodiments, a plurality of tracking markers 318 can be mounted (or otherwise secured) thereon to an outer surface of the robot 302, such as, for example and without limitation, on base 306 of robot 302, on robot arm 304, or on the end-effector 312. In exemplary embodiments, at least one tracking marker 318 of the plurality of tracking markers 318 can be mounted or otherwise secured to the end-effector 312. One or more tracking markers 318 can further be mounted (or otherwise secured) to the patient 320. In exemplary embodiments, the plurality of tracking markers 318 can be positioned on the patient 320 spaced apart from the surgical field 326 to reduce the likelihood of being obscured by the surgeon, surgical tools, or other parts of the robot 302. Further, one or more tracking markers 318 can be further mounted (or otherwise secured) to the surgical tools (e.g., drill, screwdriver, dilator, implant inserter, or the like). Thus, the tracking markers 318 enable each of the marked objects (e.g., the end-effector 312, the patient 320 and the surgical tools) to be tracked by the robot 302. In exemplary embodiments, system 300 can use tracking information collected from each of the marked objects to calculate the orientation and location, for example, of the end-effector 312, the surgical instrument (e.g., positioned in the tube 314 of the end-effector 312), and the relative position of the patient 320.

The markers 318 may include radiopaque or optical markers. The markers 318 may be suitably shaped include spherical, spheroid, cylindrical, cube, cuboid, or the like. In exemplary embodiments, one or more of markers 318 may be optical markers. In some embodiments, the positioning of one or more tracking markers 318 on end-effector 312 can maximize the accuracy of the positional measurements by serving to check or verify the position of end-effector 312. Further details of surgical robot system 300 including the control, movement and tracking of surgical robot 302 and of a surgical instrument can be found in U.S. Patent Publication No. 2017/0239007, which is incorporated herein by reference in its entirety for all purposes.

Exemplary embodiments include one or more markers 318 coupled to the surgical instrument. In exemplary embodiments, these markers 318, for example, coupled to the patient 320 and surgical instruments, as well as markers 318 coupled to the end-effector of the robot 302 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 318 can comprise conventional reflective spheres capable of being tracked using a commercially available optical tracking system such as Polaris Spectra. Polaris Spectra is also a registered trademark of Northern Digital, Inc. In one embodiment, the markers 318 coupled to the end-effector 312 are active markers which comprise infrared light-emitting diodes which may be turned on and off, and the markers 318 coupled to the patient 320 and the surgical instruments comprise passive reflective spheres.

In some embodiments, light emitted from and/or reflected by markers 318 can be detected by camera 322 and can be used to monitor the location and movement of the marked objects. In alternative embodiments, markers 318 can comprise a radio-frequency and/or electromagnetic reflector or transceiver and the camera 322 can include or be replaced by a radio-frequency and/or electromagnetic transceiver.

FIG. 22 illustrates surgical robot system 300 with robot 302 and camera stand 324, in a docked configuration. Robot 302 includes display 310, upper arm 303, lower arm 304, end-effector 312, vertical column 308, casters 330, cabinet 332, tablet drawer 334, connector panel 336, control panel 338, and ring of information 340. FIG. 22 illustrates the surgical robot system 300 in a docked configuration where the camera stand 324 is nested with the robot 302, for example, when not in use. It will be appreciated by those skilled in the art that the camera 322 and robot 302 may be separated from one another and positioned at any appropriate location during the surgical procedure, for example, as shown in FIG. 21. One or more of the following U.S. Patent Publications describe suitable robotic and/or navigation systems in more detail: 2017/0079727; 2017/0007334; 2017/0172669; 2017/0239007; 2016/0256225; 2016/0278875; and 2016/0220320. These publications and any others identified herein are incorporated by reference in their entireties for all purposes.

Figure 23:
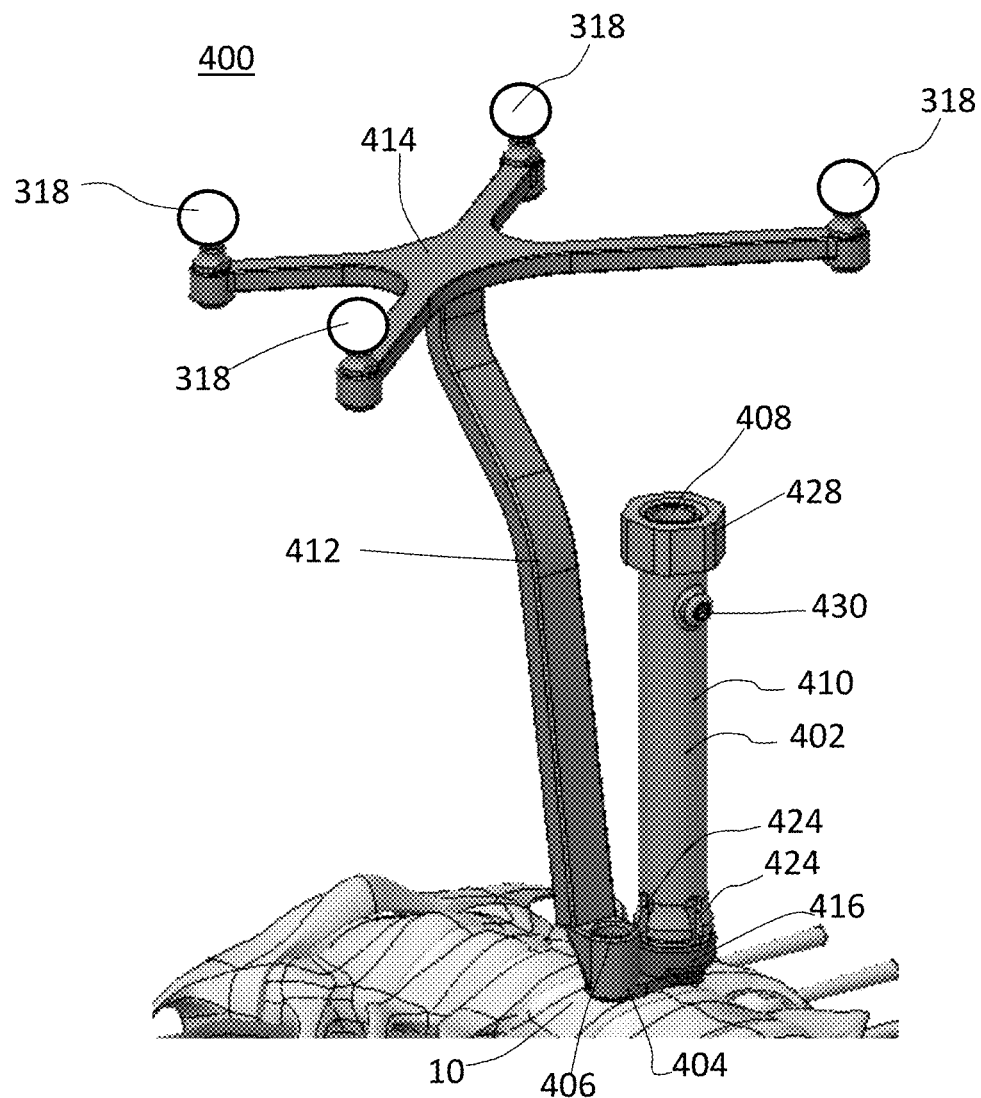
FIG. 23 is a perspective view of a stable reference array and a polyaxial drill guide configured to be used with navigation and/or a robot guidance system.
Figure 24:
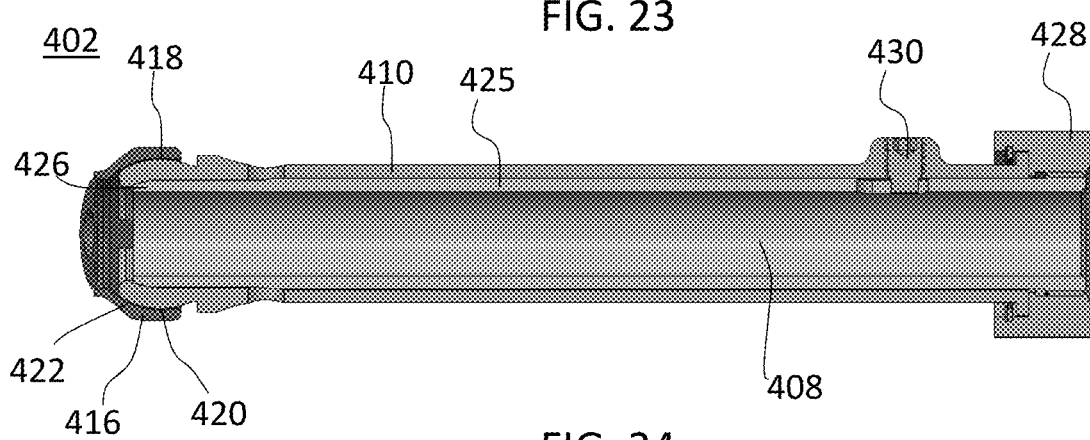
FIG. 24 is a close-up view of the polyaxial drill guide of FIG. 23.

Turning now to FIGS. 23-24, one or more specialized devices may further improve the robotics system and/or navigation for use with the transcorporeal microdecompression procedure. One challenge with navigation and robotics is having a stable reference array. FIG. 23 depicts a patient reference array, dynamic reference base (DRB), or array 400 that anchors directly to the vertebral body 10. The array 400 may include one or more markers 318 configured to be tracked by camera 322 such that robot 302 can identify and determine the position and movement of the markers 318 in three-dimensions in real time. Array 400 may include a variable angle drill guide 402, similar to uniplanar drill guide 50 or fixed angle drill guide 150 described herein, such that one or more instruments (e.g., drills) may be guided along a trajectory to create and/or access channel 14 in the vertebra 10.

The array 400 may include a base 404 having one or more surfaces configured to engage with the anatomy of the anterior surface of the vertebra 10. The base 404 may be placed flush with and centered on the anterior wall of the patient's vertebral body 10. Similar to uniplanar drill guide 50 or fixed angle drill guide 150, the base 404 may be anchored in place, for example, through a first opening 406 with a temporary fixation screw, pin, or other fastener 54. The base 404 may include a second opening configured to be aligned with the lumen 408 through guide tube 410. The base 404 may be anchored in place, additionally or alternatively, for example, with one more spikes 75 protruding downwardly from the base 404.

An extension arm 412 may extend from the base 404 and may be configured to hold a fixed array 414 of markers 318. The extension arm 412 may be curved or contoured to keep the array 414 out of the working area of the guide tube 410. The array 414 and placement of markers 318 may be selected such that the robot 302 knows the type of array 400, instrument, and/or procedure to be performed. Although four fixed markers 318 are exemplified in array 414, it will be appreciated that any suitable number and placement of markers 318 may be used.

The array base 404 may include a ball joint 416 for a polyaxial drill guide 410 to attach to. The ball joint 416 may be used with navigation while the standalone array 400 could be used a robot guidance system, whose arm 304 could hold the trajectory of the instrument (e.g., drill).

As best seen in FIG. 24, the variable angle drill guide 402 may be used to set the trajectory with navigation and lock the selected trajectory between pilot drilling, channel drilling, and/or any other operations while drilling the main trajectory. The base 404 is attached to the vertebral body with a fixation screw 54. The ball joint 416 defines a spherical hole 418 and the guide 410 has a matching sphere 420 at tip 422 that fits into the hole 418, for example, due to one or more cuts 424 that allow the tip 422 to expand and/or contract. The inner sleeve 425 utilizes a tapered tip 426 to force the sphere 420 into contact with the base, thus locking the ball joint 416 and the corresponding drill trajectory. The proximal end 428 of the guide 402 contains a locking mechanism that may include a threaded set screw or pin 430, for example. Alternatively, the locking mechanism may include a ratcheting sleeve to allow forward locking motion but resist loosening, a lever/cam mechanism similar to a bicycle wheel clamp, or of other suitable design to lock the trajectory of the guide tube 410.

Using robotic and/or navigation for creating the initial channel trajectory helps minimize the amount of manual flaring out to access the pathology, thus preserving more bone towards the posterior wall of the vertebral body and minimizing the time of burring/cutting bone. Better targeting with robotics and/or navigation may also allow for safer channel creation for patients with abnormal physiology.

The patient reference array or dynamic reference base (DRB) 400 with attached adjustable guide tube 402 may be rigidly mounted to the vertebral body 10 and then registered with the robot 302. After which, the adjustable guide tube 410 may be used to perform the transcorporeal microdecompression procedure. It is contemplated that this array 400 may also have one or more linear adjustment mechanisms to allow offset of the entry point of the adjustable guide tube 410. One linear adjustment mechanism to adjust the rostrocaudal entry point may be adequate since the surgeon may be able to assess the correct entry position laterally, or no linear adjustment mechanism may be necessary if there is a range of acceptable positions for performing the procedure and the surgeon can successfully position the device to be somewhere within this range.

The robot 302 may utilize interoperative and/or preoperative CT scans and/or MRI images. A CT (computerized tomography) uses multiple x-rays, taken at different angles, to produce the cross-sectional imaging. An MRI (magnetic resonance imaging) uses magnetic fields and radio frequencies to produce the imaging. According to one embodiment, workflow for a navigated procedure using the DRB/drill guide 400 and intraoperative CT may be as follows:

1. Expose the anterior cervical spine and attach the DRB/drill guide tool 400 with two or more screws 54 into the vertebral body 10 or adjacent vertebral bodies. Rough feedback on best location to attach the device could be direct visualization or fluoroscopy.
2. Temporarily mount an ICT (intra-op CT registration) fixture or an outrigger with radio-opaque fiducials 318 at a known location near the DRB 400.
3. Collect an intraoperative CT scan using O-arm or other imaging device.
4. Register tracking to the ICT and transfer this registration to the DRB. Remove the ICT.
5. With registration complete, insert a navigated tool into the guide tube 410. With guide tube unlocked, angle the navigated tool while watching CT image slices in planes defined by the navigated tool until the desired trajectory is needed. Adjust the linear offsets if necessary to position the tool where needed.
6. While holding navigated tool in correct location, lock the angular and linear mechanisms on the guide tube 410.
7. At this navigated position, assess implant length and drill stop positions for the procedure.
8. Perform microdecompression procedure through the guide tube 410, navigating tools where possible.

If no linear adjustment mechanism is present, the above workflow is still possible but in Step S, the user may adjust the tube position to the best angular orientation for the procedure, understanding the constraints imposed by where the device was mounted and if necessary, removing and reattaching the device in a different location.

If preoperative CT is to be used, the workflow may differ slightly and may be as follows:

1. Expose the anterior cervical spine and attach the DRB/drill guide tool 400 with two or more screws 54 into the vertebral body 10 or adjacent vertebral bodies. Rough feedback on best location to attach the device could be direct visualization or fluoroscopy.
2. Collect a pair of fluoroscopic images with a tracked fluoroscopy unit. The tracking array on the fluoroscopy unit and the DRB array 400 may both be visible at the time each fluoro shot is collected. Register tracking to a preoperative CT or MRI by performing the bone contour matching of fluoro shots to digitally reconstructed radiographs.
3. With registration complete, insert a navigated tool into the guide tube 410. With guide tube unlocked, angle the navigated tool while watching CT/MRI image slices in planes defined by the navigated tool until the desired trajectory is needed. Adjust the linear offsets if necessary to position the tool where needed.
4. While holding navigated tool in correct location, lock the angular and linear mechanisms on the guide tube 410.
5. At this navigated position, assess implant length and drill stop positions for the procedure.
6. Perform microdecompression procedure through the guide tube, navigating tools where possible.

By utilizing surgical planning software, navigation and robotics, it may be easier and safer to prepare the access channel 14, size the bone plug 20, and insert the bone plug 20 than may be possible using hand tools and fluoroscopy.

Figures 25, 26:
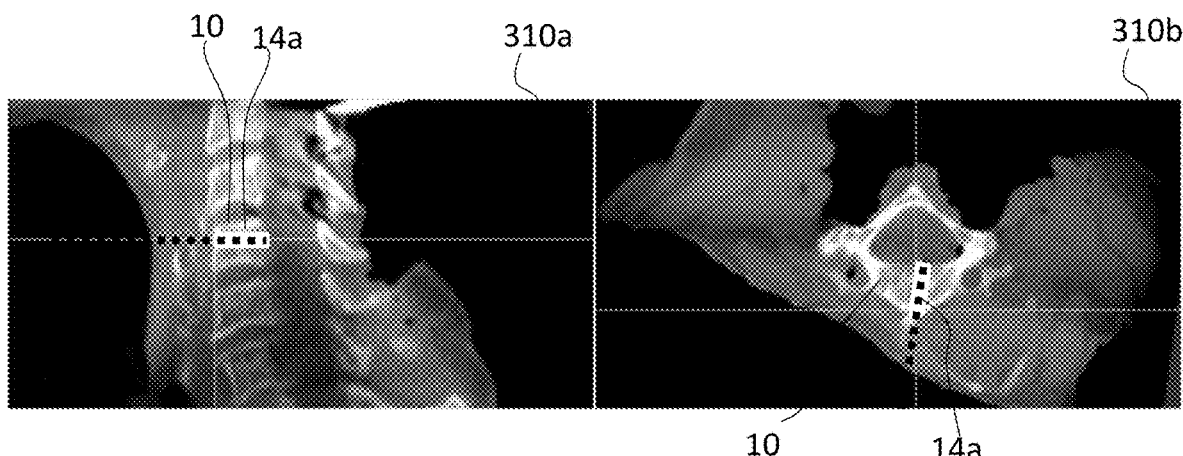
FIG. 25 depicts a sagittal view of a CT scan with computer graphics overlaid to help the user plan the location, orientation, and trajectory of an access channel through one or more vertebrae according to one embodiment.
FIG. 26 depicts an axial view of the CT scan of FIG. 25.

In some further embodiments, navigated robotics and software tools can augment or replace a drill guide. Turning now to FIGS. 25-26, one software tool could allow the surgeon to virtually select the location and orientation of the diagonal channel 14 through the vertebra 10 on a CT or MRI image 310a, 310b, for example.

FIG. 25 shows a sagittal view 310a of a CT scan and FIG. 26 shows an axial view 310b of a CT scan with computer graphics overlaid to help the user plan the trajectory for the planned access channel 14a to the cervical spinal canal. Axes corresponding to true rostrocaudal, lateral, and anteroposterior directions are drawn on the CT slices and the displayed planes intersect the planned channel 14a. In one embodiment, the diameter of the channel 14a may be fixed at 6 mm, and there may be a fixed lateral angulation of 7.5° relative to midline of the planned channel 14a. It will be appreciated that the trajectory, position, and orientation of the planned channel 14a may be modified or moved by the surgeon during pre-planning or in real time during the surgical procedure.

In yet another embodiment, the software tools may be used in conjunction with the uniplanar drill guide 50, for example. FIGS. 27-30 show an embodiment of a software feature that may allow the user to select the appropriate tooth or detent for the uniplanar drill guide 50 from the surgical planning screen 310 of the robot 302. The user adjusts the placement of the foot of the drill guide 50 relative to the spine or that placement is auto-set based on image processing and as the user adjusts the slice plane, the corresponding drill guide position is displayed.

The software tools may assist in pre-planning or during surgery to aid in selection of the desired notch of the tooth array 80 on the uniplanar guide 50. As best seen in FIGS. 27-30, an adjustable interface allows the user to select the angle of the planned channel 14a through the vertebra 10, and then provides feedback on the appropriate notch on the uniplanar drill guide 150. Feedback could be visual, showing a representation 80a of the tooth array 80 and specific notch where the tool should be set, or could be numerical, specifying the notch number that the drill guide 150 should be set to. Such a software interface also allows the implant length to be selected and the distance from entry to spinal canal to be accurately measured, allowing the lockable depth stop 200 to be accurately set, for example.

In yet further embodiments, through navigated robotics, the drill guide could be eliminated and instead, the robot 302 could hold a guide tube 314 at the necessary location for the surgeon to drill through. Surgical planning could be similar to FIGS. 25-26 but once the location of the implant is set, the robot 302 may automatically position itself adjacent to the surgical site in the correct location and orientation to allow drilling and device insertion. Software can enable the robot 302 to automatically position the guide tube 314 along the required trajectory but away from the patient by the exact amount so that the drill or other tool "bottoms out" once the appropriate depth is reached. This feature is an additional safety measure to prevent accidentally drilling into the spinal canal. A drill or insertion tool with tracking array may allow the user to watch the location of the drill and the position of the implant during drilling and implant placement respectively.

To prevent skiving of the drill tip along the bone surface when creating the access channel 14, it may be desirable for the drill guide to remain in contact with the anterior bony surface of the spine during drilling. It is therefore contemplated that a lockable drill guide, similar to drill guide 200, may be utilized. The drill guide may have an adjustable telescoping mechanism whose function is to set the amount by which the drill can exit the bottom of the guide tube when the drill housing contacts the proximal end of the drill guide. The drill guide may be sized so that its outer diameter is in close tolerance with the inner diameter of the robot's guide tube. The entire drill guide may then slide through the robot's guide tube 314 and the surgeon may proceed with drilling, aware that the drill will bottom out on the nested guide tube when target depth is reached. Additionally, the depth of the tool may be navigated and displayed on the robotic system 300.

According to yet further embodiments, the robot 302 may further assist with the transcorporeal microdecompression. A potentially challenging portion of the transcorporeal microdecompression procedure is placement of the graft after decompression is complete. Forcing the graft into place may require malleting, which may be dangerous in the patient's exposed neck region. It is contemplated that the robot 302 could assist in placement of a graft. The robot's guide tube 314 may serve as a mechanism to redirect applied force to be only along the trajectory of the drilled channel, even if the actual force is applied is off angle. The robot 302 may channel the force in such a way because of its rigidity and floor mounting. A driving tool inserted through the guide tube 314 held by the robot 302 may apply force only in the direction of the channel 14, even if struck off-angle by the surgeon, since the forces directed in other axes may be absorbed by the robot arm 303, 304. As described above, the driving tool inserted through the guide tube 314 can utilize the proximal end of the guide tube 314 as a depth stop, preventing the surgeon from inadvertently driving the implant 20 too deep.

One skilled in the art will appreciate that the embodiments discussed above are non-limiting. While devices may be described as suitable for a particular location (e.g., vertebra) or approach, one skilled in the art will appreciate that the devices, instruments, and methods described herein can be used for multiple locations and approaches. In addition to the devices, instruments, and methods described above, one skilled in the art will appreciate that these described features can be used with a number of other implants and instruments, including fixation plates, rods, fasteners, and other orthopedic devices. It will also be appreciated that one or more features of one embodiment may be partially or fully incorporated into one or more other embodiments described herein.

What is claimed is:

1. A system for performing transcorporeal microdecompression, the system comprising:
an extending from a first end to a second end, the first end configured to be inserted into a channel in a vertebra, the second end having an opening, the implant further comprising a tapered side wall connecting the first and second ends, and a graft window extending through the side wall;
an inserter having an outer sleeve, a middle sleeve terminating in a tip, the middle sleeve positioned within the outer sleeve, an inner shaft positioned within the middle sleeve, and an actuator configured to move the middle sleeve axially along a length of the inserter, wherein the tip is configured to mate with the opening in the implant such that when the actuator pushes the middle sleeve forward, the tip is compressed, but when moved back, the inner shaft forces the tip outward, thereby mating with the opening of the implant; and
a uniplanar drill guide having a base with a tooth array, a fastener configured to temporarily secure the base to the vertebra, a guide tube movable relative to the base, the guide tube having a central lumen configured to guide an instrument to create or access the channel in the vertebra, wherein movement of the guide tube is controllable by an actuation mechanism having a rotating lock arm with a cam surface and a selector pin movable by the cam surface, wherein the selector pin is configured to engage with one or more teeth of the tooth array on the base to thereby lock an angle of the guide tube.

2. The system of claim 1 further comprising a robotic navigation system configured to determine a pre-planned angle for the guide tube of the uniplanar drill guide.

3. The system of claim 1, wherein the implant is a bone void plug made of allograft.

4. The system of claim 1, wherein the tip of the middle sleeve and the opening in the second end of the implant form a circular dovetail joint.

5. The system of claim 1, wherein the base of the uniplanar drill guide includes a first extension portion and a second extension portion connected by a bridge portion.

6. The system of claim 5, wherein the first extension portion extends upwardly and terminates in a first free end, the first free end having a t-shape, and the tooth array is positioned on an upper surface of the first free end.

7. The system of claim 5, wherein the second extension portion extends upwardly and terminates in a second free end, the second extension portion defining a partially cylindrical cavity configured to guide the fastener into position.

8. The system of claim 5, wherein the base of the uniplanar drill guide includes one or more indentations along the bridge portion.

9. The system of claim 1, wherein the base of the uniplanar drill guide includes one or more spikes protruding downwardly from the base.

10. The system of claim 1, wherein the actuation mechanism further includes a linearly moveable pin controllable by a button.

11. The system of claim 10, wherein the rotating lock arm includes a first portion and a second portion provided substantially perpendicular to one another, the first portion having an elongate opening for receiving the moveable pin and the second portion having the cam surface configured to move the selector pin.

12. A uniplanar drill guide for performing transcorporeal microdecompression comprising:
a base having a first extension portion and a second extension portion connected by a bridge portion, wherein the first extension portion extends upwardly and terminates in a first free end, the first free end having a t-shape, and a tooth array positioned on an upper surface of the first free end, wherein the second extension portion extends upwardly and terminates in a second free end, the second extension portion defining a partially cylindrical cavity;
a fastener configured to temporarily secure the base to a vertebra; and
a guide tube movable relative to the base, the guide tube having a central lumen configured to guide an instrument to create or access the channel in the vertebra,
wherein movement of the guide tube is controllable by an actuation mechanism having a rotating lock arm with a cam surface and a selector pin movable by the cam surface, wherein the selector pin is configured to engage with one or more teeth of the tooth array on the base to thereby lock an angle of the guide tube.

13. The guide of claim 12, wherein the actuation mechanism further includes a linearly moveable pin controllable by a button.

14. The guide of claim 13, wherein the rotating lock arm includes a first portion and a second portion provided substantially perpendicular to one another, the first portion having an elongate opening for receiving the moveable pin and the second portion having the cam surface configured to move the selector pin.

15. A surgical robot system comprising:
an array having a base configured to temporarily affix to a vertebra, and an extension arm extending from the base and terminating in a fixed array having a plurality of markers, the array further including a guide tube and a ball joint connecting the guide tube to the base, the ball joint defines a spherical hole and the guide tube has a matching sphere that mates with the spherical hole, wherein when the ball joint is locked, an angle of the guide tube is locked, thereby forming a targeted trajectory through the guide tube;
a robot configured to track and/or navigate the array, the robot having a camera configured to track the plurality of markers, the robot configured to determine the location and movement of the markers;
wherein the guide tube includes an inner sleeve having a tapered tip configured to force the sphere open, thereby locking the ball joint and the targeted trajectory.

16. The system of claim 15, wherein the guide tube has a central lumen configured to receive one or more instruments that are guided along the targeted trajectory.

17. The system of claim 15, wherein the extension arm is curved to keep the fixed array out of the working area of the guide tube.

18. The system of claim 15, wherein the sphere of the guide tube includes a plurality of cuts that allow the sphere to expand and contract.

19. The system of claim 15, wherein the robot includes a software program configured to determine a pre-planned angle for the guide tube using one or more pre-operative CT scans.

* * * * *